United States Patent [19]

Buscemi et al.

[11] Patent Number: 5,693,034
[45] Date of Patent: Dec. 2, 1997

[54] LUBRICOUS POLYMER NETWORK

[75] Inventors: Paul J. Buscemi, Long Lake; Paul C. Slaikeu, Vadnais Heights, both of Minn.

[73] Assignee: SciMed Life Systems, Inc., Maple Grove, Minn.

[21] Appl. No.: 458,557

[22] Filed: Jun. 2, 1995

Related U.S. Application Data

[63] Continuation of Ser. No. 140,704, Oct. 21, 1993, abandoned, which is a continuation of Ser. No. 809,889, Dec. 18, 1991, abandoned.

[51] Int. Cl.$^6$ ............................ A61K 9/14; A61M 25/00; A61M 25/10
[52] U.S. Cl. ........................... 604/265; 604/96; 424/486
[58] Field of Search ............................ 424/486; 604/265, 604/96

[56] References Cited

U.S. PATENT DOCUMENTS

| | | | |
|---|---|---|---|
| 3,566,874 | 3/1971 | Shepherd | 128/349 |
| 3,886,947 | 6/1975 | Sawyer | 128/348 |
| 3,895,169 | 7/1975 | Wichterle | 428/420 |
| 3,975,350 | 8/1976 | Hudgin et al. | 260/30.4 |
| 4,119,094 | 10/1978 | Micklus et al. | 128/132 |
| 4,279,795 | 7/1981 | Yamashita et al. | 260/29.6 |
| 4,371,686 | 2/1983 | Yamamoto et al. | 528/76 |
| 4,373,009 | 2/1983 | Winn | 428/424 |
| 4,423,184 | 12/1983 | Kopolow et al. | 525/57 |
| 4,459,317 | 7/1984 | Lambert | 427/2 |
| 4,496,535 | 1/1985 | Gould et al. | 424/19 |
| 4,521,564 | 6/1985 | Solomon et al. | 525/54.1 |
| 4,616,057 | 10/1986 | Lindemann et al. | 524/458 |
| 4,729,914 | 3/1988 | Kliment et al. | 428/36 |
| 4,740,207 | 4/1988 | Kreamer | 623/1 |
| 4,798,847 | 1/1989 | Roesink et al. | 521/50 |
| 4,822,615 | 4/1989 | Iwata et al. | 424/423 |
| 4,857,579 | 8/1989 | Domeier | 524/507 |
| 4,906,237 | 3/1990 | Johansson et al. | 604/265 |
| 4,931,287 | 6/1990 | Bae et al. | 424/484 |
| 5,026,607 | 6/1991 | Kiezulas | 428/423.7 |
| 5,079,093 | 1/1992 | Akashi et al. | 424/411.1 |
| 5,192,617 | 3/1993 | Stofko et al. | 428/411.1 |

FOREIGN PATENT DOCUMENTS

WO86/01813  3/1986  WIPO.

OTHER PUBLICATIONS

Brynda et al 1987 Biomaterial Jan. pp. 57–60.
Mueller et al Gradient Drug Delivery Agents vol. 27, pp. 4043–4064 1982.
Brynda et al., "Polyethylene/Hydrophilic Polymer Blends for Biomedical Applications", *Biomaterials*, vol. 8, pp. 57–60, (Jan. 1987).
Weathersby et al., "Fibrinogen Adsorption to Surfaces of Varying Hydrophilicity", *Journal of Bioengineering*, vol. 1, pp.395–409, (1977).
Okano et al., "Hydrophilic–Hydrophobic Microdomain Surfaces Having an Ability to Suppress Platelet Aggregation and Their *In Vitro* Antithrombogenicity", *Journal of Biomedical Materials Research*, vol. 20, pp. 919–927, (1986).
Grainger et al. "*In Vitro* and *Ex Vivo* Platelt Interactions With Hydrophilic–Hydrophobic Poly(ethylene oxide)–Polystyrene Multiblock Copolymers", *Journal of Biomedical Materaisl Research*, vol. 23, pp. 979–1005, (1989).
Mueller et al, "Gradient–IPN–Modified Hydrogel Beads: Their Synthesis by Diffusion–Polycondensation and Function as Controlled Drug Delivery Agents", *Journal of Applied Polymer Science*, vol. 27, pp. 4043–4064, (1982).

*Primary Examiner*—P. F. Kulkosky
*Attorney, Agent, or Firm*—Vidas, Arrett & Steinkraus, P.A.

[57] ABSTRACT

A polymer network useful as a lubricous coating, the polymer network comprising a reaction product of a vinyl prepolymer and an uncrosslinked hydrogel retained within the reaction product such that the network exhibits a greater lubricity when wet.

7 Claims, No Drawings

LUBRICOUS POLYMER NETWORK

This application is an FWC application Ser. No. 08/140,704 filed Oct. 21, 1993, now abandoned which is an FWC application Ser. No. 07/809,889 filed Dec. 18, 1991, now abandoned.

BACKGROUND OF THE INVENTION

The present invention relates to a composition for forming a polymer network, and in particular, it relates to a polymer network useful as a lubricous coating.

Lubricity of medical devices, such as catheters that are insertable into the body is an important feature. One method of increasing lubricity is to apply a lubricous coating to the surface of the catheter.

Silicone has been used as a coating for many olefin and metallic medical devices. However, silicone is hydrophobic, and although imparting some lubricity against certain surfaces, silicone's coefficient of friction increases dramatically in the presence of water, plasma, or blood.

Hydrogel polymers have also been used in coatings. Hydrogels are characterized by an initial tacky quality followed by lubricity upon hydration. Many hydrogel compositions hydrate virtually instantaneously, while others require considerably more time.

The Lambert U.S. Pat. No. 4,459,317 describes a process for coating a polymer surface with a hydrophilic coating with low friction in a wet condition. The process includes applying to the polymer surface a solution containing between 0.05 to 40 percent of the compound, which comprises at least two unreacted isocyanate groups per molecule, evaporating the solvent, applying a solution containing between 0.05 to 50 percent of polyethylene oxide to the treated polymer surface and then evaporating the solvent. The coating is then cured at an elevated temperature.

The Johannson et al U.S. Pat. No. 4,906,237 describes a hydrophilic coating that is made by applying a solution of an osmolality increasing compound to a non-reactive hydrophilic polymer surface layer and then evaporating the solvent of the solution.

The Bae et al U.S. Pat. No. 4,931,287 describes a heterogeneous interpenetrating polymer network for use in the controlled release of drugs. The network is a heterogeneous matrix in one instance using polyethylene oxide crosslinked with for example a triisocyanate, as a hydrophilic component with styrene, an alkyl methacrylate, or a polytetramethylene ether glycol as the hydrophobic component.

SUMMARY OF THE INVENTION

The present invention includes a polymer network comprising a vinyl polymer and an uncrosslinked hydrogel retained within the vinyl polymer. The present invention also includes a method of making such a polymer network including a vinyl polymer and an uncrosslinked hydrogel.

The present invention also includes a lubricous coating secured to the surface of a device insertable within the living body and to a process of applying such a coating to the device. The process includes applying to the surface a solution containing an uncrosslinked hydrogel and a vinyl prepolymer along with a polymerization initiator, and then polymerizing the vinyl prepolymer such that the hydrogel is retained within the polymerized vinyl polymer. Preferably, the surface of the device is treated prior to application of the coating solution.

The present invention also includes a drug delivery system comprising a coating secured to a device insertable into a living body wherein the coating comprises an uncrosslinked hydrogel secured to the device by a vinyl polymer. The drug can be permanently entrapped in the coating or can be leachable from the coating into the living body upon hydration.

DETAILED DESCRIPTION OF THE PREFERRED EMBODIMENTS

The present invention includes a polymer network comprising a vinyl polymer and an uncrosslinked hydrogel retained within the vinyl polymer that is useful as a high lubricity coating. The high lubricity coating is useful on devices that are insertable within living tissue.

By "polymer network" is meant two polymers synthesized such that the polymer chains are intertwined within each other. There is no apparent carbon-to-carbon chemical bonding between the polymers except perhaps only accidental covalent bonding. The intertwining of the polymers is of a permanent nature rendering the polymers physically inseparable from each other.

The polymer network of the present invention is formed as a lubricous coating by application of a mixture of an uncrosslinked hydrogel, a vinyl prepolymer, and a free radical initiator in a solvent to an active, activated or "primed" substrate. By prepolymer is meant monomers or oligomers or both used as reactants to form a polymer. The three primary constituents of the mixture are applied preferably as a single component and cured as a single system to form the polymer network of the present invention. The reaction of the vinyl prepolymer on the substrate in the presence of the uncrosslinked hydrogel produces the polymer network.

By hydrogel is meant a substance that when exposed to water and used as a coating is characterized by a decrease in its coefficient of friction or an increase in its lubricity. Suitable hydrogels for use in the present invention are uncrosslinked hydrogels, and include polyethylene oxide, polyacrylic acid, polyacrylamide, poly(sodium4-styrenesulfonate), poly(3-hydroxybutyric acid), polyvinylpyrrolidone, and 2-hydroxyethyl methacrylate.

The hydrogel of the present invention is preferably a high molecular weight hydrogel. The high molecular weight of the hydrogel provides at least two advantages. First, it ensures sufficient entanglement with the vinyl polymer such that the hydrogel does not leach out of the polymer network. Second, although the high molecular weight ensures that the hydrogel is unextractable from the polymer network, smaller molecules such as drugs ensnared within the hydrogel can leach out. A crosslinked hydrogel would, on the other hand, entrap a drug and prevent leaching. The extent of entrapment of the hydrogel is also dependent on the crosslink density of the vinyl polymer. In the case of polyethylene oxide, molecular weights in the range of 50,000 to 100,000 and above are most suitable.

By vinyl polymer is meant those polymers produced by chain reaction polymerization. Suitable vinyl polymers for use in the present invention include methyl methacrylate and other mono-functional acrylates, diacrylates, glyceryl propoxy triacrylate and other tri-functional acrylates, styrene and other vinyl monomers, including divinyl benzene and other divinyl polymers. One example of a diacrylate suitable in the present invention is neopentyl glycol diacrylate (NPG). Other diacrylates suitable in the present invention include ethylene glycol di(meth)-acrylate, 1,3-propylene glycol di(meth)acrylate, 1,4-butanediol di(meth)acrylate, 1,6-hexanediol di(meth)acrylate, diethylene glycol di(meth)

acrylate, triethylene glycol di(meth)acrylate, tetraethylene glycol di(meth)acrylate, polyethylene glycol di(meth)acrylate, and neopentyl glycol di(meth)acrylate.

In preparing the solution mixture of the present invention, the hydrogel is mixed with the vinyl prepolymer in a solvent. In one preferred embodiment, isopropyl alcohol in combination with water acts as a suitable solvent. Water alone has also been used as a solvent. In one embodiment, a preferred ratio of polyethylene oxide to a diacrylate prepolymer is 10:1. Lower ratios of polyethylene oxide to prepolymer have also been found to be suitable.

Crosslinking is facilitated by a small amount of a free radical initiator added to the mixture. When a diacrylate is used, the mole ratio of free radical initiator to the diacrylate is $10^4:1$. To further facilitate crosslinking, oxygen should be degassed from the solution since oxygen inhibits free radical reactions. One preferred method of degassing the oxygen is through the use of nitrogen bubbling.

Next, the mixture is applied to a substrate. A variety of surfaces act as suitable substrates. For example, the mixture may be applied to wood, metal, polymers or the like. If the mixture is applied to a polyethylene surface such as on a catheter, preferably the surface of the catheter is glow discharge plasma treated. Other polymeric substrates, such as polyimides containing diaromatic ketones and polyethylene terephthalate, have also been found to be suitable substrates even when not plasma treated. Polyurethanes and nylons are primed with a vinyl functional isocyanate. Metals, such as stainless steel and gold, require a primer such as a vinyl or acrylate functional silane for best adhesion.

The coated surface is then cured. The coated film is exposed to heat or UV light for a short period of time. The heat or UV light triggers the polymerization and crosslinking of the prepolymer. Preferably, the mixture is cured using a high intensity ultraviolet lamp. The precise amount of time needed to cure the surface is dependent on the source of energy, the relative amounts of constituents in the composition, the thickness of the coating desired, and other factors. Generally, the amount of time required for thermal cure is from about 1 to 30 minutes. UV curing requires less time and is generally in the range of less than one minute.

A great advantage of the vinyl polymer of the present invention is its ability to adhere to a substrate that can support free radicals, or can support other species which can form free radicals, such as peroxides. The strong adherence of the vinyl polymer to the substrate aids in the prevention of unwanted material breaking off from the coating and being left in the body.

The present coating has a variety of uses in the medical device market. One apparent use is the application of the coating on various devices used within the human body. In the preferred embodiment, the coating is applied to catheters such as angioplasty catheters.

Applying the polymer network of the present invention as a coating to catheters or other medical devices has a number of advantages. First, the coating of the present invention is highly lubricous when wet. In the dry state, the coating is virtually indistinguishable from the substrate. In contrast, silicone, which is widely used in devices such as catheters, and when acting as the coating is very noticeable in the dry state and often is more tacky when wet.

Second, as mentioned previously, the coating of the present invention can be applied to a variety of different substrates with strong adherence. Thus, the polymer network of the present invention provides a lubricous, as well as an adherent and durable coating. Vigorous rubbing and long-term hydration do not reduce the coating's lubricity, demonstrating the strong adhesion of the coating.

Third, the polymer network of the present invention is useful as a drug delivery system. By varying such parameters as hydrogel molecular weight and crosslink density of the vinyl polymer, an additional constituent, such as a drug, can be incorporated into the present polymer network. In one preferred embodiment, heparin is used as the drug. The drug is entrapped in the polymer network and leaches out of the coating when the coating is wet delivering the heparin to immediately adjacent areas of the body. The advantages of incorporating a drug which is released from the coating on medical devices is apparent. Effects of thrombus formation, restenosis, infections, and even disease transmission could be minimized or eliminated through the use of the coating of this invention.

Fourth, as mentioned previously, the present invention includes a polymer network in which the hydrogel, such as polyethylene oxide, is virtually entrapped within the system. Entrapment prevents unwanted material from leaving the coating and entering the body. Coatings which remain intact and do not deposit undesired materials are generally preferred to erodible coatings, such as silicone coatings, which might have the capacity to induce a response from the body. The coating of the present invention leaves no unwanted foreign material within the body.

The following examples are illustrative only and are not intended to limit the present invention. The examples are submitted in order to demonstrate more explicitly the process and composition of the present invention.

EXAMPLE 1

20 grams of a 5 percent solution of an uncrosslinked polyethylene oxide (PEO) from Aldrich Chemical Co., (a hydrogel) having an average molecular weight of 900,000 was mixed with 0.10 grams of neopentyl glycol diacrylate (NPG) from Sartomer Co., of Pennsylvania in a solution containing 18 grams of water and 71 grams of isopropyl alcohol (IPA). 0.8 grams of a 0.001 percent solution of azobisisobutronitrile (AIBN) in isopropyl alcohol was added to the solution. The mole ratio of azobisisobutronitrile to neopentyl glycol diacrylate was $10^4:1$. Oxygen was removed from the solution by bubbling nitrogen through the solution.

The solution was then applied to a film of plasma treated polyethylene (PE). The wet coated film was then exposed to a 1500 watt ultraviolet (UV) source for 40 seconds at a distance of nine inches. The film was rinsed with running water. The resulting surface was highly lubricous and dramatically different than the uncoated surface. Vigorous rubbing did not reduce the coating lubricity, nor was there noticeable residue on the fingers. Dry or wet storage did not reduce the wet lubricity.

EXAMPLE 2

A solution of PEO and NPG in IPA and water was prepared as in Example 1. 10 mg of heparin was dissolved in 1 ml water. 1 ml of IPA was added to the heparin water mixture, with resulting cloudiness indicating heparin precipitation. Several drops of 1% lecithin (a surfactant) in chloroform was added to the heparin mixture until the solution was clarified. The heparin mixture was then added to the PEO/NPG/AIBN solution such that the ratio of PEO:NPG:heparin was 50:5:1. The solution was applied to a plasma treated PE film and cured as in Example 1. The resulting coating had similar characteristics as the coating of Example 1. A detectable quantity of heparin was found using infrared spectroscopy in residue resulting after 15 minutes of rinsing of the coating.

EXAMPLE 3

A solution of PEO and NPG in IPA and water containing heparin was prepared as in Example 2. The solution was applied to approximately nine inches of the distal end of a SKINNY angioplasty catheter manufactured by SciMed Life Systems, Inc., of Maple Grove, Minn. The catheter, prior to application of the solution, was plasma treated. The catheter was cured using the procedure of Example 2 but with manual turning of the catheter to insure direct exposure to UV of all surfaces of the coating. The resulting catheter had similar characteristics as the coating of Example 2.

EXAMPLE 4

The procedure of Example 1 was followed except that tripropylene glycol diacrylate from Sartomer Co., of Pennsylvania was used in place of the neopentyl glycol diacrylate. A similar highly lubricous coating was produced. The coating withstood vigorous rubbing and did not leave a noticeable residue on the fingers.

EXAMPLE 5

The procedure of Example 1 was followed except that trifunctional triacrylate ester from Sartomer Co., of Pennsylvania was substituted for neopentyl glycol diacrylate. A similar highly lubricous coating was produced. The coating withstood vigorous rubbing and did not leave a noticeable residue on the fingers.

EXAMPLE 6

The procedure of Example 1 was followed except that polyethylene glycol 200 diacrylate from Sartomer Co., of Pennsylvania was substituted for neopentyl glycol diacrylate. A similar highly lubricous coating was produced. The coating withstood vigorous rubbing and did not leave any noticeable residue on the fingers.

EXAMPLE 7

The procedure of Example 1 was followed except that divinyl benzene from Dow Chemical of Michigan was substituted for neopentyl glycol diacrylate. A similar highly lubricous coating was produced. Vigorous rubbing did not reduce the coating lubricity, and the coating did not leave any noticeable residue on the fingers.

EXAMPLE 8

The procedure of Example 1 was followed except that methylmethacrylate from Fisher Scientific of New Jersey was substituted for neopentyl glycol diacrylate. A similar highly lubricous coating was produced. Vigorous rubbing did not reduce the coating lubricity, and no noticeable residue was left on the fingers.

EXAMPLE 9

The procedure of Example 1 was followed except that 8 parts of methylmethacrylate (Fisher Scientific of New Jersey) to 2 parts of divinyl benzine (Dow Chemical of Michigan) was substituted for the neopentyl glycol diacrylate. A similarly highly lubricous coating was produced. Vigorous rubbing did not reduce the coating lubricity and no noticeable residue was left on the fingers.

EXAMPLE 10

The procedure of Example 1 was followed except that 1 gram of polyacrylic acid from Aldrich Chemical Co., of Wisconsin having an average molecular weight of 250,000 was used as the hydrogel. 2 grams of 5 percent neopentyl glycol diacrylate solution in isopropyl alcohol was mixed with the hydrogel. 0.80 grams of 0.001 percent azobisisobutronitrile solution was then added.

The resulting surface was highly lubricous. Vigorous rubbing did not reduce the coating lubricity nor was there noticeable residue on the fingers.

EXAMPLE 11

The procedure of Example 1 was followed except that 6.0 grams of poly(sodium 4-styrene sulfonate) having an average molecular weight of 70,000 from Aldrich Chemical Co., of Wisconsin was mixed with 2 grams of a 5 percent solution of neopentyl glycol diacrylate made by Sartomer Co., of Pennsylvania in isopropyl alcohol. 0.8 grams of a 0.001 percent solution of azobisisobutronitrile was added to the solution.

The resulting coating was highly lubricous and dramatically different than the uncoated surface. Vigorous rubbing did not reduce the coating lubricity nor was there noticeable residue on the fingers.

EXAMPLE 12

The procedure of Example 1 was followed except that i gram of polyvinyl pyrolidone made by BASF Corp., of New Jersey was used as the hydrogel. The polyvinyl pyrolidone was mixed with 2 grams of 5 percent neopentyl glycol diacrylate from Sartomer Co., of Pennsylvania in an isopropyl alcohol solution. 0.80 grams of a 0.001 percent azobisisobutronitrile initiator was added to the solution.

The resulting coating was highly lubricous and dramatically different than the uncoated surface. Vigorous rubbing did not reduce the coating lubricity nor was there noticeable residue on the fingers.

EXAMPLE 13

The procedure of Example 12 was followed except that the solvent used was an isopropyl alcohol/toluene solvent instead of the water/isopropyl alcohol solvent. A similarly highly lubricous coating was produced.

Although the present invention has been described with reference to preferred embodiments, workers skilled in the art will recognize that changes may be made in form and detail without departing from the spirit and scope of the invention.

What is claimed is:

1. An angioplasty catheter including a composition coating the distal end of said catheter, the composition comprising:

the reaction product of vinyl monomers selected from the group consisting of mono-, di- and tri-acrylates, styrene, and divinyl benzene said monomers being polymerizable to form a crosslinked polymer that adheres to the surface of the device and resists degradation from rubbing and hydration;

a polymerization initiator;

and an uncrosslinked linear, water-soluble, hydrophilic hydrogel selected from the group consisting of polyethylene oxide, polyacrylic acid, polyacrylamide, poly(sodium-4-styrenesulfonate), poly(3-hydroxybutyric acid), polyvinylpyrrolidone and 2-hydroxyethyl methacryate, said hydrogel being intertwined with the polymer so as to prevent the hydrogel from leaching out of the coating composition, the hydrogel being lubricous when wet and substantially unnoticeable on the surface when dry, and said monomers being polymerized in the presence of the hydrogel; and a solvent.

2. An angioplasty catheter including a drug delivery system coating the distal end of said catheter, said drug delivery system comprising:

a reaction product of vinyl monomers selected from the group consisting of mono-, di- and tri-acylates, styrene and divinyl benzene, said monomers being polymerizable to form a crosslinked polymer that is adherent to a substrate on a medical device and resistant to degradation from rubbing and hydration;

with an uncrosslinked linear, hydrophilic, water-soluble hydrogel selected from the group consisting of polyethyene oxide, polyacrylic acid, polyacrylamide, poly(sodium-4-styrenesulfonate), poly(3-hydroxybutyric acid), polypyrrolidone and 2-hydroxyethyl methyacrylate which is lubricous where wet and substantially-unnoticeable on the substrate when dry and retained within the reaction product, said monomers being polymerized in the presence of the hydrogel; and a drug miscible in water, and leachable from the coating.

3. A catheter for insertion into a human body, the catheter comprising:

(a) a shaft having a proximal and a distal and a lumen extending from proximal end to the distal end, wherein the distal end will be inserted into the human body, and (b) a polymer network disposed on a surface of the shit, the polymer network comprising a polymer formed by reacting of a vinyl monomer selected from the group consisting of mono-, di, and tri-acylates, styrene and divinyl benzene, with an uncrosslinked linear, hydrophilic, water-soluble hydrogel selected from the group consisting of polyethylene oxide, polyacrylic acid, polyacrylamide, poly(sodium-4-styrenesulfonate), poly(3-hydroxybutyric acid), polyvinylpyrrolidone and 2-hydroxyethyl methacrylate which is lubricous when wet and substantially-unnoticeable on the substrate when dry and retained within the reaction product, said monomers being polymerized in the presence of the hydrogel.

4. The catheter of claim 3 further comprising a guide wire lumen, having a proximal end and a distal end, disposed within the shaft.

5. The catheter of claim 4 further comprising a balloon having a proximal end and a distal end, the proximal end of the balloon being secured to the distal end of the shaft and the distal end of the balloon being secured to the distal end of the guide wire lumen.

6. The catheter of claim 5 wherein the polymer network is disposed on the balloon.

7. A medical device for insertion into a human body, the device comprising:

(a) an elongate member having a proximal end and a distal end, wherein the distal end will be inserted into the human body, and (b) a polymer network disposed on a surface of the elongate member, the polymer network comprising a polymer formed by reacting a vinyl monomer selected from the group consisting of mono-, di- and tri-acrylates, styrene and divinyl benzene, with an uncrosslinked linear, hydrophilic, water-soluble hydrogel selected from the group consisting of polyethylene oxide, polyacrylic acid, polyacrylamide, poly(sodium-4-styrenesulfonate), poly(3-hydroxybutyric acid), polyvinylpyrrolidone and 2-hydroxyethyl methacrylate which is lubricous when wet and substantially-unnoticeable on the substrate when dry and retained within the reaction product, said monomers being polymerized in the presence of the hydrogel.

* * * * *

UNITED STATES PATENT AND TRADEMARK OFFICE
CERTIFICATE OF CORRECTION

PATENT NO. : 5,693,034

DATED : Dec. 2, 1997

INVENTOR(S) : PAUL J. BUSCEMI ET AL

It is certified that error appears in the above-identified patent and that said Letters Patent is hereby corrected as shown below:

Col. 7, line 31, after "distal" insert -- end --;

Col. 7, line 34, delete "shit" and insert -- shaft --.

Signed and Sealed this

Third Day of March, 1998

Attest:

BRUCE LEHMAN

Attesting Officer        Commissioner of Patents and Trademarks